United States Patent [19]

West

[11] Patent Number: 5,443,847

[45] Date of Patent: Aug. 22, 1995

[54] SPECIFIC DETOXIFICATION OF URUSHIOL WITH MANGANESE SALTS

[76] Inventor: Philip W. West, 605 Nelson Dr., Baton Rouge, La. 70808

[21] Appl. No.: 92,129

[22] Filed: Jul. 15, 1993

[51] Int. Cl.6 .................. A61K 33/32; A61K 31/28
[52] U.S. Cl. .................... 424/639; 514/492; 514/862; 424/401; 424/DIG. 6
[58] Field of Search ............... 424/45, 639, DIG. 6, 424/401; 514/862

[56] References Cited

U.S. PATENT DOCUMENTS

| | | | |
|---|---|---|---|
| 3,071,508 | 1/1963 | Strauss . | |
| 3,749,772 | 7/1973 | Cardarelli | 424/81 |
| 3,862,331 | 1/1975 | Crary | 424/331 |
| 3,875,301 | 4/1975 | Windheuser | 424/45 |
| 3,875,391 | 4/1975 | Windheuser | 424/45 |
| 3,922,342 | 11/1975 | Rathbun | 424/79 |
| 4,002,737 | 1/1977 | Borris | 424/94 |
| 4,199,575 | 4/1980 | Gunther | 424/217 |
| 4,259,318 | 3/1981 | Duke et al. | 424/94.4 |
| 4,428,965 | 1/1984 | Elsohly et al. | 424/311 |
| 4,663,151 | 5/1987 | Waali | 424/45 |
| 4,863,897 | 9/1989 | Dede et al. | 514/6 |
| 5,008,119 | 4/1991 | Matsubara | 424/639 |
| 5,232,709 | 8/1993 | Saitman et al. | 424/630 |

Primary Examiner—Thurman K. Page
Assistant Examiner—Neil Levy
Attorney, Agent, or Firm—Roy, Kiesel & Tucker

[57] ABSTRACT

A method for treating rhus dermatitis caused by exposure to urushiol is provided, comprising the step of topically applying a therapeutically effective amount of a soluble manganese salt to the affected area of the skin. The manganese compound penetrates the pores of the skin and acts a chelating agent on the urushiol molecule, deactivating its toxicity. A detoxification agent for urushiol is also provided, comprising a composition containing a soluble salt of manganese, such as an aqueous or alcohol solution, wherein the weight percent of manganese in said composition is a therapeutically effective amount, such as between 0.01% and 10.0% manganese. The detoxification agent is also useful as a means of preventing rhus dermatitis when applied to the skin in an appropriate base.

2 Claims, No Drawings

SPECIFIC DETOXIFICATION OF URUSHIOL WITH MANGANESE SALTS

BACKGROUND OF THE INVENTION

1. Field of the Invention

This invention relates to the prevention or treatment and cure of dermatitis caused by contact with poison ivy, poison oak, poison sumac, and related plants containing urushiol compounds.

2. Description of the Prior Art

Poison ivy, poison oak, and poison sumac all belong to a family of plants referred to as Anacardiaceae, which are well-known for their toxic effects on mammals. The active toxin in these plants is an organic compound known as urushiol. Urushiol usually comprises a 1,2-dihydroxy benzene (catachol) with an alkane side chain consisting of 11–19 carbon atoms, and having either zero, one or three points of unsaturation, depending on the plant source. When one of these plants makes contact with the skin, the urushiol penetrates the surface of the skin and often results in a condition referred to as rhus dermatitis, manifesting itself symptomatically as skin irritation, inflammation and blistering. Many attempts have been made over the years to solve this problem, and there have been varying levels of success. Virtually all of the remedies fall into one of three types: (1) using soap and water or other organic solvents to remove the toxic compound, (2) using barrier creams to prevent allergens from contacting the skin, and (3) using detoxicants to chemically react with and neutralize the urushiol. Under the third type of treatment, upon which this invention focuses, most prior art methods have concentrated on points of unsaturation in the alkane side chain of the urushiol molecule with attempts at oxidation. However, limited success has been achieved through such efforts, prompting the inventor herein to reconsider the problem by using one of several common and safe metal salts as a means of deactivating the urushiol through chelation and thus alleviating and even curing its physiological effects.

Using a detoxicant on the urushiol present in the skin carries the benefits of eliminating the cause of the rhus dermatitis. However, while many different chemicals can possibly be used as a detoxicant, there are very few which satisfy the requirements of being highly effective, fast-acting, easy to obtain and administer, non-irritating to the skin, and inexpensive to produce. Therefore, a treatment for rhus dermatitis is desired which can deactivate the toxic urushiol, and which is easily applied through the use of a pharmaceutically acceptable preparation. The inventive detoxicant is intended to be applied topically in either an aqueous, alcohol, or other polar solvent, but can also be used in conjunction with a number of other products. A nonexclusive list of other applications would be insect repellants, sun screen lotions, camouflage colorings, as well as antiseptic and anesthetic ointments and sprays to reduce dermatitis symptoms. Additionally, the detoxicant would prove beneficial as part of a vanishing cream base as a means of preventing urushiol contact with the skin.

SUMMARY OF THE INVENTION

It is an object of this invention to provide a detoxification agent for urushiol which is effective in deactivating the toxicity of urushiol.

It is another object of this invention to provide a detoxification agent for urushiol which does not irritate the skin.

Another object of this invention is to provide a detoxification agent for urushiol which is easy to obtain and inexpensive for the consumer.

Yet another object of this invention is to provide a detoxification agent which can be topically applied through a wide variety of pharmaceutically acceptable preparations.

Therefore, a method for treating rhus dermatitis caused by exposure to urushiol is provided, comprising the step of applying to an area of skin affected by said rhus dermatitis a composition comprising a therapeutically effective amount of a soluble manganese salt to react with the urushiol to form a non-toxic, inactive chelate. A detoxification and curative agent for urushiol is also provided, comprising a composition containing a soluble salt of manganese, wherein the weight percent of manganese in said composition is a therapeutically effective amount.

DESCRIPTION OF THE PREFERRED EMBODIMENTS

Organic molecules having carboxyl (—COOH) and hydroxyl (—OH) groups offer available reaction sites for polyvalent metals. Urushiol has two such hydroxyl groups, so that divalent metals, such as Manganese II, can replace the hydrogens of the functional groups to form a ring as shown below.

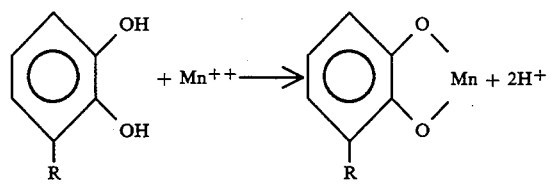

Where R is the alkane side chain. Such ring products, called chelates, often have great stability, especially where the ring size is determined by five or six atoms. Thus, in the urushiol molecule, a divalent metal can replace the hydrogens to form a stable five-atom ring.

Several compounds containing manganese may be used to achieve the detoxifying effect of the urushiol molecule. In particular, soluble salts of manganese such as $MnSO_4$, $MnSO_4$ hydrate, $MnCl_2$, $MnCl_2 \cdot 4H_2O$, $Mn(C_2H_3O_2)_2$, $Mn(C_2H_3O_2)_2 \cdot 4 H_2)$, and $Mn(CHO_2)_2 \cdot H_2O$ have been found effective. The products of the reaction between the urushiol and the manganese compound will of course depend on the particular salt employed.

Although there are other divalent and trivalent metals which would work equally well as a chelating agent to deactivate the urushiol toxicity, such as aluminum, iron, lead, calcium, magnesium, cadmium, zinc, nickel, and beryllium, manganese is preferred because it appears to be most effective and carries no known undesirable side effects. For example, when aluminum chlorohydrate is used as a chelating agent, the astringent properties of this compound prevail and the pores become constricted. This action serves to obstruct the path needed for the chelating agent to reach the urushiol within the skin. While this compound may be useful in preventing the urushiol toxin from entering the pores, it does not work well as a treatment method.

Also, aluminum chlorohydrate and other trivalent metal salts must typically have a pH of less than pH 5 to prevent the metal from hydrolyzing and precipitating. Once precipitation takes place, the products are non-reactive with the urushiol. Therefore, because of the high acidity required to keep it in solution, aluminum chlorohydrate is ill-suited for use on sensitive areas of the skin and around the eyes. Salts of iron and lead, such as ferric chloride and lead nitrate, may also be used as chelating agents, but these also tend to be acutely toxic. Furthermore, the use of iron salts can create a brown lesion or "tattoo" in the affected skin area, making it unacceptable. Dangers associated with toxicity also preclude the use of zinc and cadmium. Calcium and magnesium salts can be used, but do not result in a stable complex to sufficiently deactivate the urushiol toxicity.

Manganese, on the other hand, is an element whose trace amounts are a necessary part of good human nutrition. There are no known adverse health effects of using this element for topical applications, so its possibility for use as an over-the-counter medication is greatly enhanced. Also, soluble salts of manganese can be administrable in a form having a pH more closely matched with the skin (but typically no greater than pH 7 to prevent hydrolyzation) so that it can be used around sensitive areas. Finally, manganese is inexpensive to obtain, resulting in lower costs of treatment than present methods.

When used as a treatment method, the manganese-based detoxicant is preferably delivered topically in a therapeutically effective amount to the site on the skin affected by rhus dermatitis, and may be used as part of an aqueous or alcohol solution. Through experimentation, the inventor has discovered that about 0.01% to 10.0% by weight of manganese in the solution is required for effective deactivation of urushiol toxicity, with the preferred amount being about 0.5 % manganese in solution. The amount of manganese is therapeutically effective when symptoms such as itching and inflammation at the affected site subside within one or two hours. When the detoxicant is used as a preventative measure, it can be mixed in similar proportions with a vanishing cream base and applied liberally to exposed skin areas. As described earlier, the detoxicant can be used prophylactically in combination with other products, including insect repellents, sun screen products, camouflage colorings, as well as antiseptic and anesthetic agents.

Although the present invention has been described in terms of specific embodiments, it is anticipated that alterations and modifications thereof will no doubt become apparent to those skilled in the art. It is therefore intended that the following claims be interpreted as covering all such alterations and modifications as fall within the true spirit and scope of the invention.

I claim:

1. A method for treating thus dermatitis caused by exposure to urushiol, comprising the step of applying to an area of skin affected by said thus dermatitis an aqueous solution consisting essentially of a therapeutically effective amount of a soluble manganese salt;

wherein said soluble manganese salt is selected from the group consisting of $MnSO_4$, $MnSO_4$ hydrate, $MnCl_2$, $MnCl_2 \bullet 4H_2$), $Mn(C_7H_3O_2)_2$, $Mn(C_2H_3O_2)_2 \bullet 4H_2$), and $Mn(CHO_2)_2 \bullet H_2O$;

wherein said aqueous solution contains 0.01% to 10.0% by weight of manganese; and wherein said aqueous solution has a pH of between pH 5 and pH 7.

2. The method according to claim 1, wherein said composition contains 0.5% by weight of manganese.

* * * * *